(12) United States Patent
Westheim

(10) Patent No.: US 7,928,114 B2
(45) Date of Patent: Apr. 19, 2011

(54) CRYSTALLINE ERLOTINIB

(75) Inventor: Raymond J. H. Westheim, Oss (NL)

(73) Assignee: Synthon BV, Nijmegen (NL)

( * ) Notice: Subject to any disclaimer, the term of this patent is extended or adjusted under 35 U.S.C. 154(b) by 213 days.

(21) Appl. No.: 11/829,482

(22) Filed: Jul. 27, 2007

(65) Prior Publication Data

US 2008/0058355 A1 Mar. 6, 2008

Related U.S. Application Data

(60) Provisional application No. 60/820,714, filed on Jul. 28, 2006.

(51) Int. Cl.
*A61K 31/517* (2006.01)

(52) U.S. Cl. ..................... 514/266.3; 544/293

(58) Field of Classification Search ............... 514/266.3; 544/293

See application file for complete search history.

(56) References Cited

U.S. PATENT DOCUMENTS 5,747,498 A 5/1998 Schnur et al.

FOREIGN PATENT DOCUMENTS

| CA | 2 302 965 A1 | 9/2000 |
| EP | 1044969 A3 | 12/2000 |
| EP | 0 817 775 B1 | 9/2001 |
| WO | WO 99/55683 | 11/1999 |
| WO | WO 01/34574 A1 | 5/2001 |
| WO | WO 2004/072049 A1 | 8/2004 |

*Primary Examiner* — James O Wilson
*Assistant Examiner* — Douglas M Willis
(74) *Attorney, Agent, or Firm* — Muncy Geissler Olds & Lowe, PLLC

(57) ABSTRACT

Crystalline Forms of erlotinib are made. The crystalline materials are useful as pharmaceutical active agents in treating various cancers as well as in forming erlotinib salts.

14 Claims, 5 Drawing Sheets

CRYSTALLINE ERLOTINIB

This application claims the benefit of priority under 35 U.S.C. §119(e) from U.S. Provisional Patent Application Ser. No. 60/820,714, filed Jul. 28, 2006, the entire contents of which are incorporated herein by reference.

BACKGROUND OF THE INVENTION

The present invention relates to crystalline erlotinib, including anhydrous as well as hydrated forms, processes for preparing them, pharmaceutical compositions thereof and their use in preparing erlotinib or pharmaceutical acceptable salts of erlotinib.

Erlotinib, chemically [6,7-bis(2-methoxyethoxy)-quinazolin-4-yl]-(3-ethynylphenyl)amine of formula 1

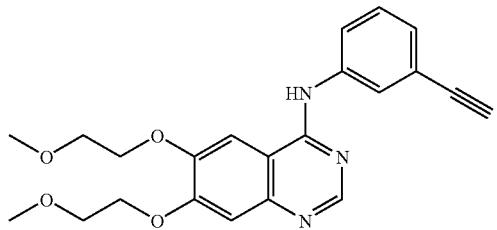

1 is a compound that inhibits the human epidermal growth factor receptor tyrosine kinase, also known as EGFR-TK, that is critical for growth of malignant cells. EGFR overexpression is associated with disease progression, and reduced survival. Erlotinib acts by blocking tyrosine kinase activity of EGFR-TK, resulting in inhibition of signaling pathway, and decreased growth of malignant tumors. Erlotinib is thus useful for the treatment of proliferative disorders such as cancers in humans. Erlotinib is marketed as its hydrochloride salt under such brand names as TARCEVA® (OSI Pharmaceuticals, Inc.) for treatment of certain lung cancers and pancreatic cancer.

WO 96/30347 and U.S. Pat. No. 5,747,498 teach quinazoline derivatives for treating hyperproliferative diseases such as cancers. Example 20 shows the formation of erlotinib free base and the subsequent conversion to the hydrochloride salt. Before the conversion to the salt, an organic phase containing the erlotinib was concentrated and the residue flash chromatographed on silica to obtain the free base as a pale yellow solid. This solid was then dissolved in a solvent and reacted with HCl to form the hydrochloride salt. There is no report of whether the solid erlotinib was crystalline.

European patent application EP 1044969 discloses processes for making erlotinib, its salts, and related compounds. Several examples make the hydrochloride salt (see examples 4, 7 and 9-11) and several make the mesylate salt (see examples 8 and 12). No mention is made in the examples of forming a solid erlotinib free base. Rather the solid forms are obtained by precipitation of the erlotinib salts.

Several patent publications disclose the existence of polymorphic forms of erlotinib salts. For example, WO 01/34574 discloses the existence of two polymorphic Forms of erlotinib hydrochloride which were designated as Form A and B. Form B is thermodynamically more stable than Form A. More recently WO 2004/072049 discloses the existence of another polymorph of erlotinib hydrochloride, designated as Form E, which is thought to have similar stability as Form B but with a higher solubility. The mesylate salt of erlotinib, with enhanced solubility compared to the hydrochloride, and its preparation is disclosed in WO 99/55683. Anhydrous erlotinib mesylate exists in three different polymorphic Forms designated Form A, B and C. Also a monohydrate of erlotinib mesylate and its use in the preparation of anhydrous mesylate Forms is disclosed.

While crystalline salts of erlotinib have been studied, it would be advantageous to be able to provide erlotinib in a solid, crystalline form.

SUMMARY OF THE INVENTION

The present invention is based on the discovery that erlotinib free base can be formed as a crystalline solid material and, more particularly, to the discovery of three specific crystalline forms. Accordingly, a first aspect of the invention relates to crystalline erlotinib free base which is substantially Form I, Form II, or Form III. The crystalline erlotinib can be an anhydrous crystal or a hydrated crystal. The crystalline erlotinib can be a stable solid material suitable for making a pharmaceutical dosage form and is thus also useful for treating hyperproliferative diseases such as cancer. Alternatively, the crystalline erlotinib can be useful in forming salts of erlotinib. For example, crystalline erlotinib free base according to the invention can be precipitated from a solution and then converted to a pharmaceutically acceptable salt such as the aforementioned hydrochloride or methanesulfonate salts. The formation of the crystalline free base can provide a useful pathway for purifying erlotinib or an erlotinib salt.

The XRPD patterns were recorded according to the following settings:

| | |
|---|---|
| Start angle (2θ): | 2.0° |
| End angle (2θ): | 35.0-50° |
| Scan step width: | 0.02° |
| Scan step time: | between 1-6 seconds |
| Radiation type: | Cu |
| Radiation wavelengths: | 1.54060 Å (Kα$_1$), primary monochromator used |
| Exit slit: | 6.0 mm |
| Focus slit: | 2 mm |
| Divergence slit: | Variable (V20) |
| Antiscatter slit: | 3.37 or 6.17 mm |
| Receiving slit: | 5.25 or 10.39 mm |

The DSC spectra were obtained according to the temperature schedule given below and the samples were measured in an aluminum pan with a pierced lit:

| | |
|---|---|
| Start temperature: | 25° C. |
| End temperature: | 260° C. |
| Heating rate: | 10° C./min |

The FT-IR spectra were obtained according to the KBr-method. The FT-IR spectra were recorded from 600 cm$^{-1}$ to 4000 cm$^{-1}$. From each FT-IR spectrum a blank FT-IR spectrum of KBr was subtracted. That blank IR spectrum was recorded prior to the measurements of the samples.

DETAILED DESCRIPTION OF THE INVENTION

Figure 4:
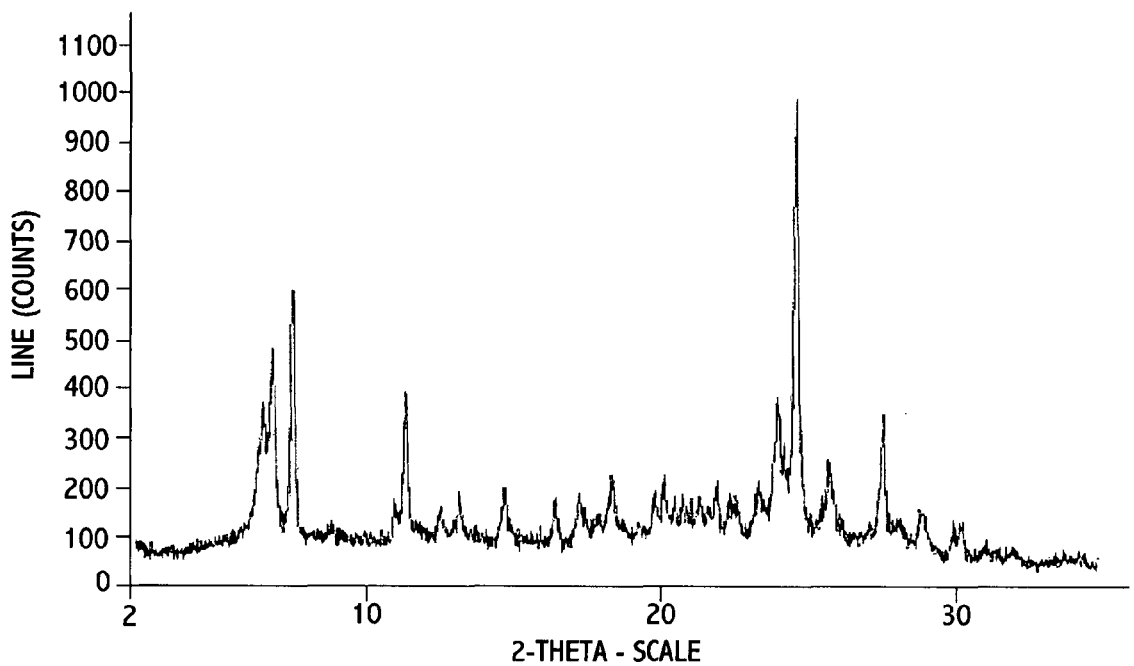
FIG. 4 is a XRPD pattern of the product of the Comparative Example

The present invention relates to the discovery of crystalline Forms of erlotinib free base. As used herein, "crystalline erlotinib" and "crystalline erlotinib free base" are used broadly to include solvates/hydrates of erlotinib as well as anhydrous forms. The crystal need not be morphologically pure but does substantially comprise one of the Forms I, II, or III. Thus the erlotinib crystalline material is "substantially" one of the Forms I, II, or III, e.g., one Form accounts for at least 80%, more typically at least 85%, and usually at least 90% of the crystalline erlotinib. A "pure" Form is substantially free of any other crystalline Forms having less than 5%, typically less than 2%, and more preferably no XRPD-detectable amount of any other crystal Form. While none of the above-mentioned prior art describes a crystalline erlotinib free base, it appears that Example 20 of WO 96/30347 may be capable of producing a type of crystalline erlotinib free base. As shown in the Comparative Example hereinafter, a similar experiment to the Example produced a material having some crystallinity as demonstrated by the XRPD shown in FIG. 4. The material has several strong peaks below 10° 2θ and may have a significant amorphous content. The crystalline portion of the material is either a different crystal From than Forms I, II and III of the present invention or is a mixture of forms; in the latter event, the crystalline erlotinib is not substantially one of Forms I, II, or III. Being able to reliably form a solid, crystalline form of erlotinib can provide useful ways of administering erlotinib. Additionally, the crystallization of the free base can serve as a useful purification step for the erlotinib base or a salt thereof, e.g., using crystalline erlotinib as the starting material for the salt formation reaction.

In general, the crystalline erlotinib free base Forms of the present invention can be formed by crystallizing erlotinib from an erlotinib solution. The solvent is generally an alcohol such as methanol, ethanol or isopropanol; acetone; acetonitrile, chloroform; 1,4-dioxane; toluene; or a mixture of two or more of these solvents. The crystallization can be induced/caused by cooling and/or adding a contrasolvent such as water or an alkane such as heptane. Other crystallization techniques may also be used, including reducing the volume of the solution by evaporation, and/or seeding.

Three specific crystalline forms have been found useful and are designated Forms I, II, and III, respectively. Forms I and III are hydrates while Form II is an anhydrate. The three forms, beginning with the anhydrous Form II, are hereafter described in more detail.

Figure 1A:
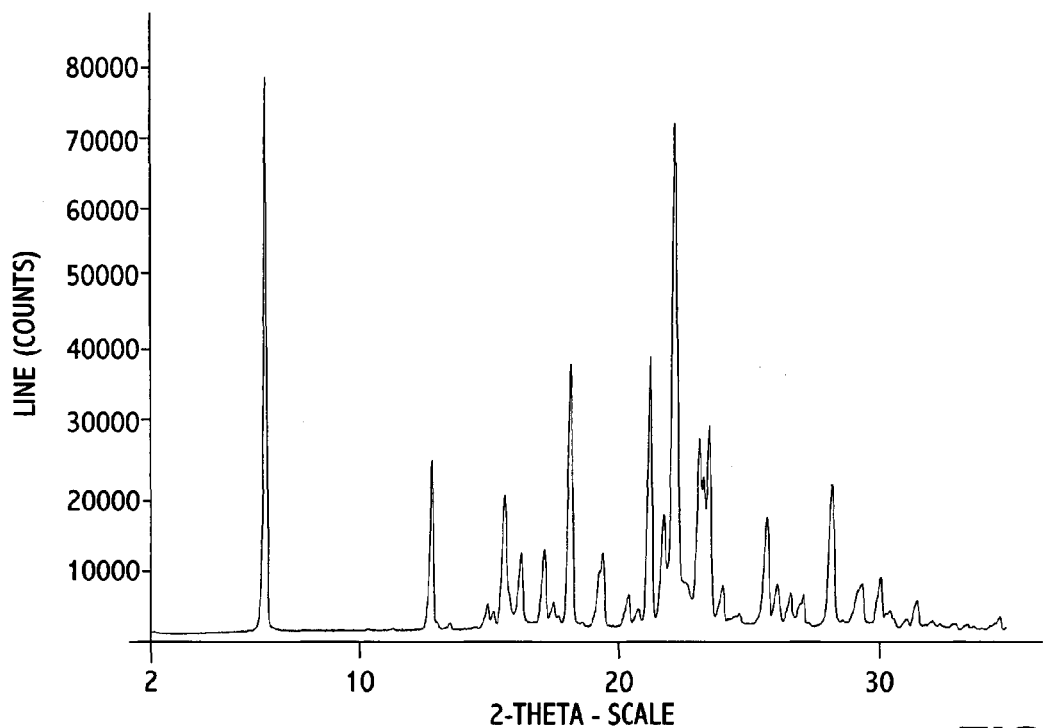
FIG. 1A is a representative XRPD pattern of erlotinib free base Form II.
Figure 1B:
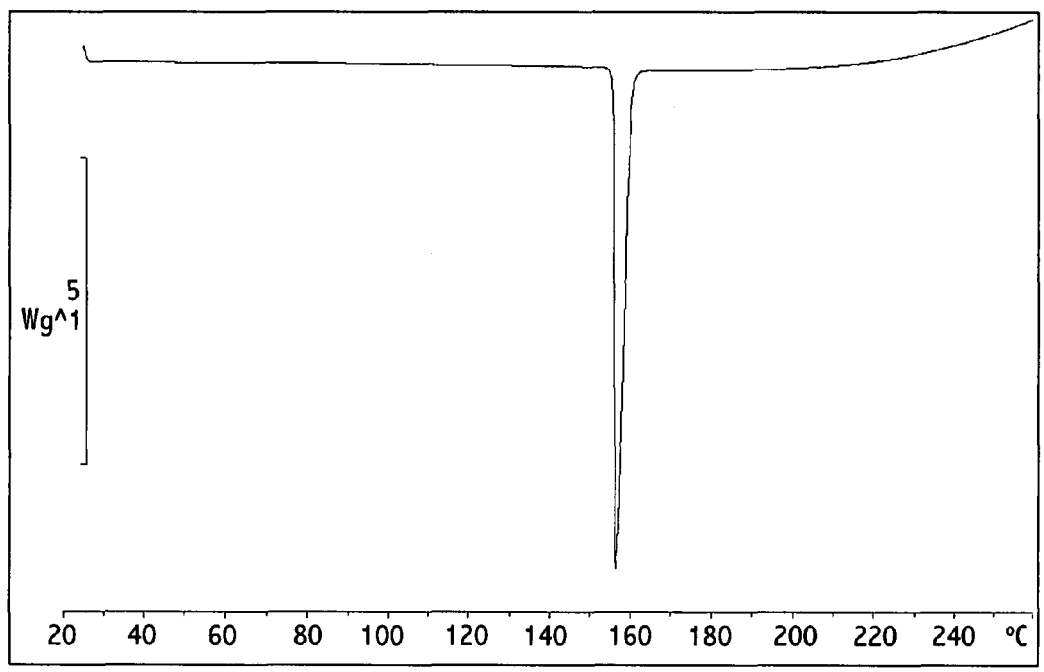
FIG. 1B is a representative DSC spectra of erlotinib free base Form II.
Figure 1C:
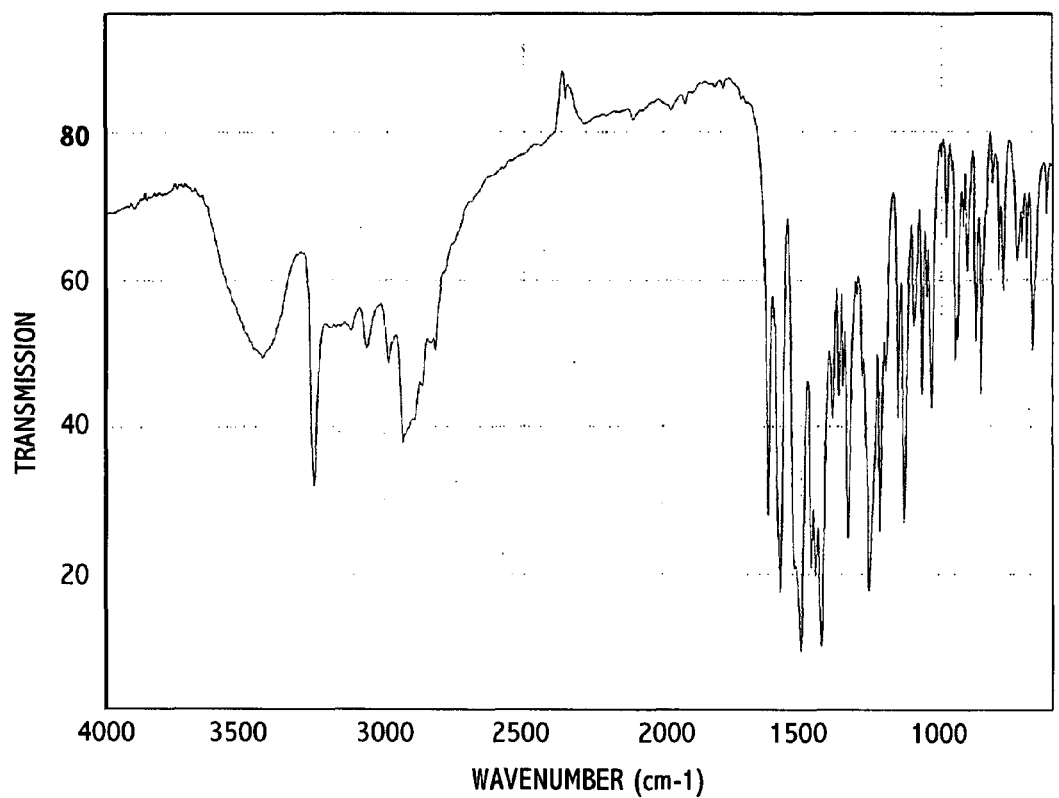
FIG. 1C is a representative FT-IR spectra of erlotinib free base Form II.

Crystalline erlotinib free base Form II of the present invention is an anhydrous crystalline form. It can generally be identified or distinguished from other erlotinib crystalline forms by the following characteristic XRPD peaks at 2θ: 6.4, 12.8, 15.6, 18.2, 22.3, 23.2, 23.6, and 25.8+/−0.2 degrees, and/or FT-IR peaks $v_{max}$ (KBr) cm$^{-1}$: 772, 851, 1033, 1131, 1218, 1256, 1334, 1430, 1502, 1576, 1619, and 3251+/−4 cm$^{-1}$. As used herein, the +/−0.2 degrees for the XRPD peaks and the 4 cm$^{-1}$ for the FT-IR peaks applies to each peak listed, respectively. Also, the listed peaks for each Form are not intended to represent an exhaustive list. Generally crystalline Form II erlotinib, in a relatively pure state, has an XRPD that substantially corresponds to FIG. 1A and/or an FT-IR that substantially corresponds to FIG. 1C. The expression "substantially corresponds" means that a pattern or spectra does not have to be superimposable over the recited figure but rather can have minor variations of the type caused by differences in sample preparation, conditions of measurement, purity of the sample to other compounds, polymorphic purity, etc., as understood by a worker skilled in the art. For example, the increase or decrease in a peak in an FT-IR spectrum corresponding to the presence of the amount of carbon dioxide gas would not indicate a different crystalline form, even though the spectra would not be superimposable.

The DSC scan of Form II shows a melting peak around 154-158° C. TGA shows only little mass loss below 180° C. Form II may be present as needles or thin plates.

When Form II is melted and cooled, no recrystallization takes place, regardless of the cooling rate or rate upon reheating. While not entirely clear, probably a stable glass is formed that does not recrystallize. Another explanation may be degradation.

XRPD under non-ambient conditions (30° C./10-90% RH and 50° C./75% RH) showed that Form II does not undergo polymorphic transitions under humid conditions at elevated temperatures. TGA confirmed that Form II can be considered non-hygroscopic.

Erlotinib base Form II can be formed by precipitating from a solution. Typically the solvent is an alcohol, especially isopropanol, or acetone. Co-solvents such as ethanol or toluene may also be present. The presence of water is generally avoided in the solution. Specific techniques include:
(i) (re)crystallization of erlotinib base from an alcoholic solvent, typically from 2-propanol; or
(ii) precipitation by adding n-heptane to a solution of erlotinib in acetone at room temperature (R.T.).

Recrystallization from 2-propanol may initially give Form II with a small amount of another Form. However, prolonged stirring results in pure Form II. This indicates that Form II is the thermodynamically more stable Form.

Mixtures of Form I and Form II were obtained by recrystallization from ethanol, toluene, 2-propanol/n-heptane (1:10 V/V), or by adding a solution of erlotinib in 2-propanol to n-heptane at 0° C. Such mixtures may be recrystallized to yield pure Form II by processes a) or b) above, if desired. Pure Form II should be understood as substantially free of any other crystalline Forms of erlotinib.

Figure 2A:
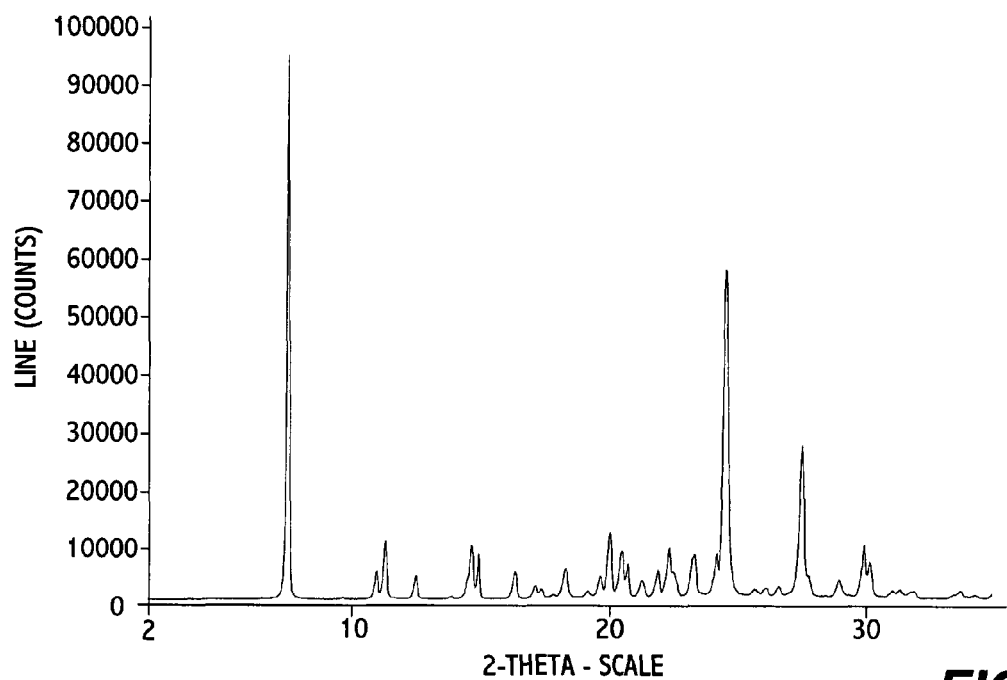
FIG. 2A is a representative XRPD pattern of erlotinib monohydrate Form I.
Figure 2B:
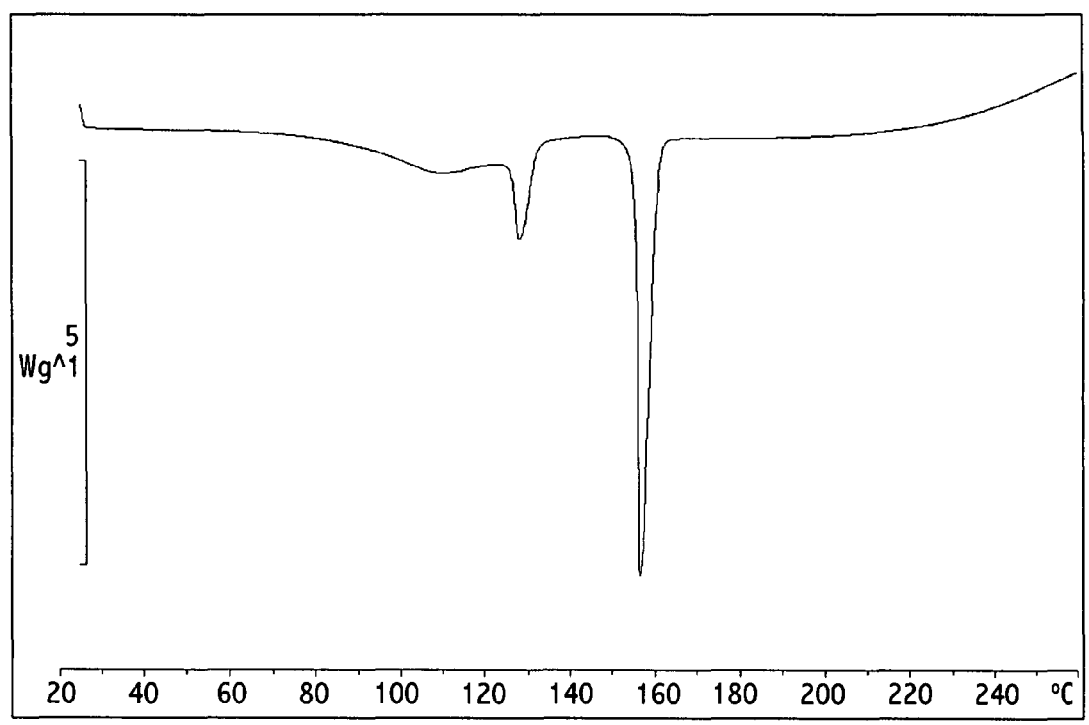
FIG. 2B is a representative DSC spectra of erlotinib monohydrate Form I.
Figure 2C:
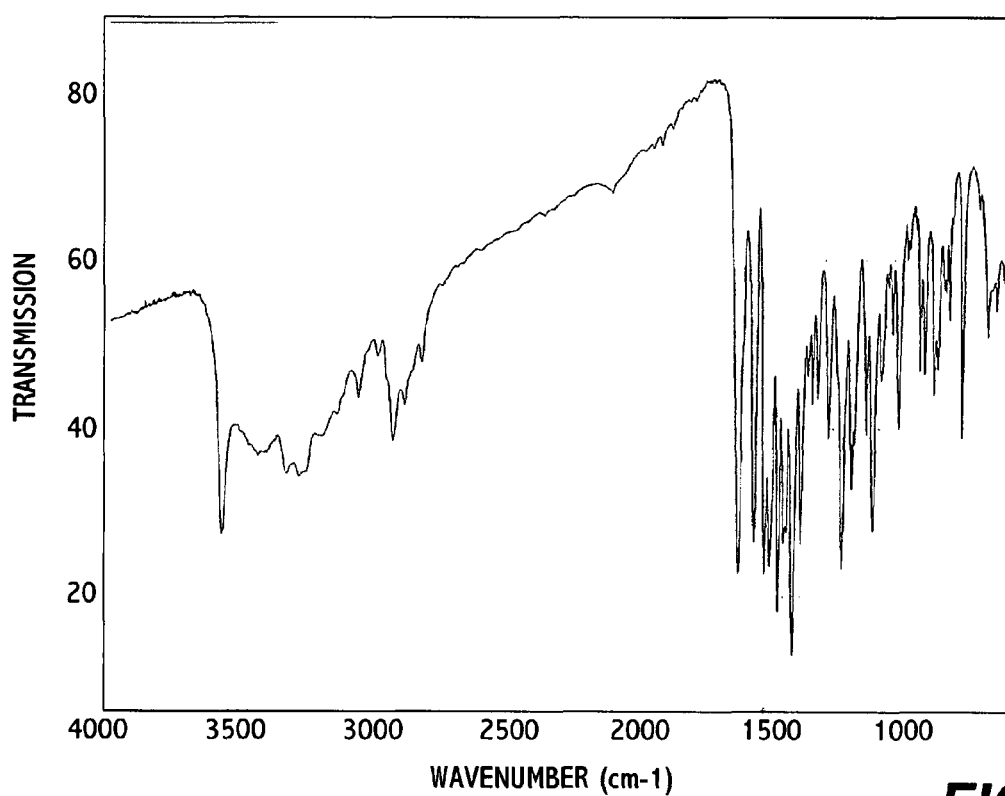
FIG. 2C is a representative FT-IR spectra of erlotinib monohydrate Form I.

Crystalline Form I is a monohydrated form of erlotinib free base that can generally be identified by the following characteristic XRPD peaks at 2θ: 7.4, 10.9, 14.6, 14.9, 18.3, 20.1, 20.5, 20.8, 22.4, 24.6, 27.6, 30.0, and 30.3+/−0.2 degrees, and/or FT-IR peaks; vmax (KBr) cm$^-$: 791, 883, 897, 1030, 1128, 1208, 1243, 1293, 1429, 1482, 1533, 1629, and 3569+/−4 cm$^{-1}$. Generally a relatively pure crystalline Form I erlotinib has an XRPD that substantially corresponds to FIG. 2A and/or an FT-IR that substantially corresponds to FIG. 2C. As used herein a "monohydrate" means that the crystalline material contains approximately 1 mole of water for each mole of erlotinib. It can vary typically by up to about 15% from a perfect 1:1 ratio. As is well known in the art, this water is bound to the crystal lattice and is not simply a wet material.

A DSC scan of Form I shows a complex evaporation endotherm below 145 C with an embedded (melting) peak around 126-129° C. Melting can be observed around 155-157° C. TGA shows evaporation of about 1 equivalent of water below 140-170° C. The crystals are well defined prisms and bars.

Figure 3A:
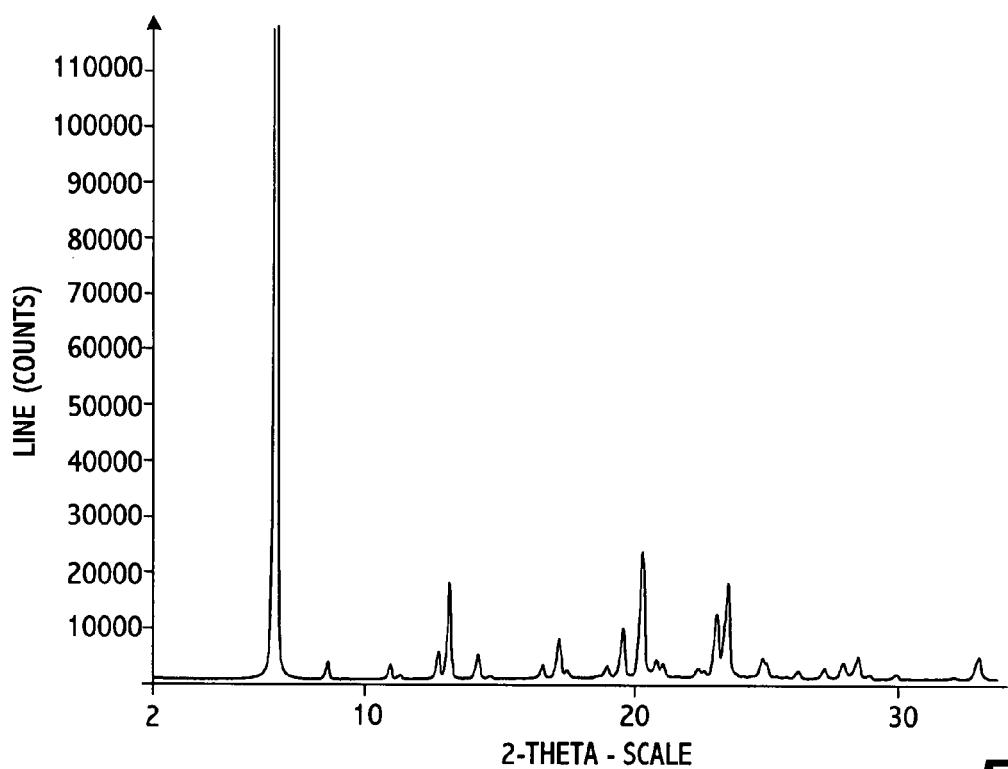
FIG. 3A is a representative XRPD pattern of erlotinib monohydrate Form III.
Figure 3B:
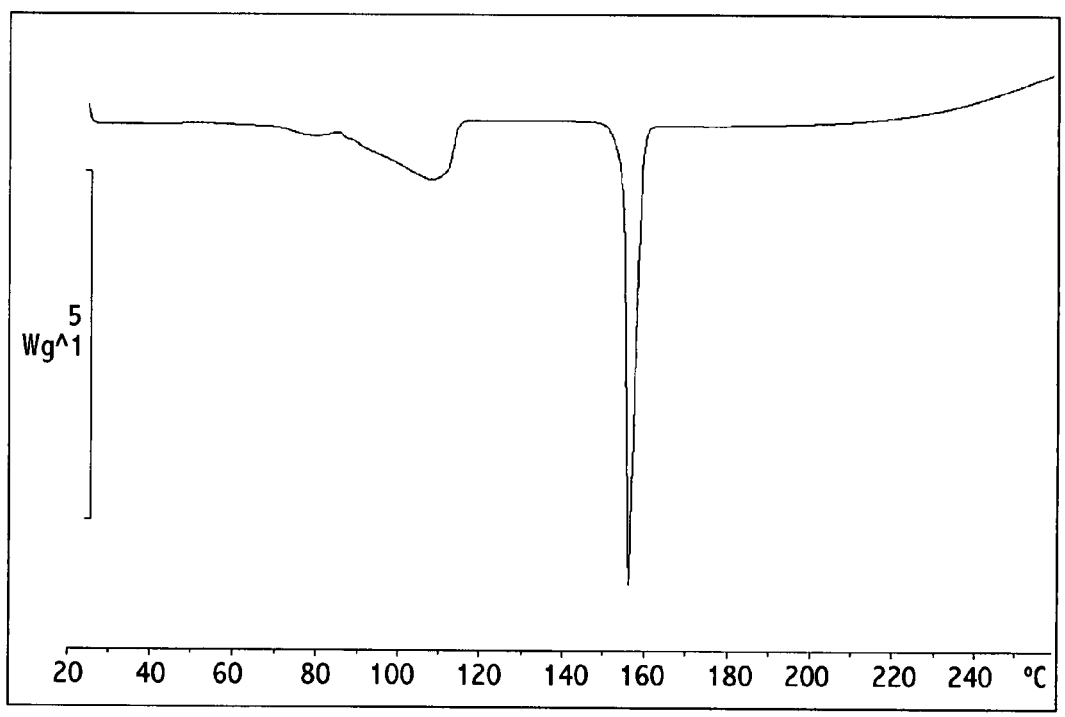
FIG. 3B is a representative DSC spectra of erlotinib monohydrate Form III.
Figure 3C:
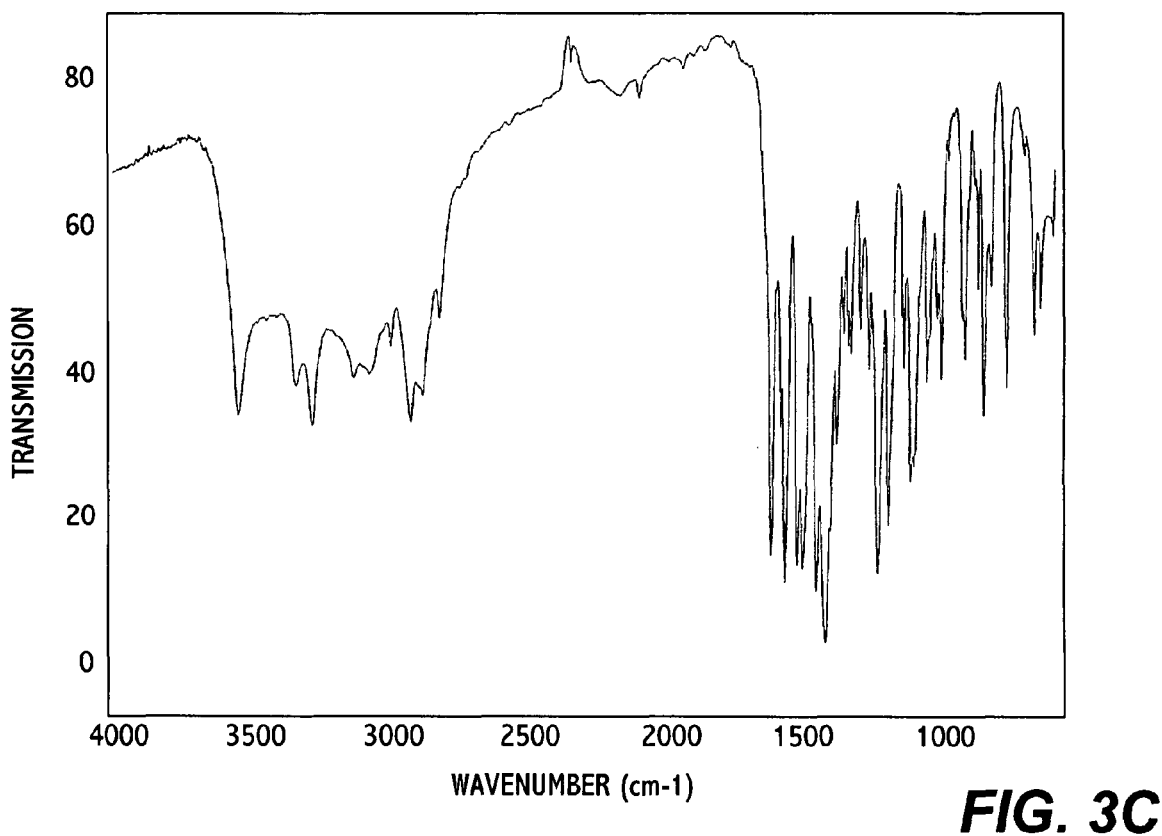
FIG. 3C is a representative FT-IR spectra of erlotinib monohydrate Form III.

Crystalline Form III is a monohydrated Form of erlotinib free base that can generally be identified by the following characteristic XRPD peaks at 2θ: 6.8, 13.1, 14.7, 20.4, 21.1, and 24.5+/−0.2 degrees and/or FT-IR peaks; vmax (KBr) cm$^{-1}$: 871, 1118, 1131, 1212, 1249, 1434, 1517, 1536, 1629, 3274, and 3536+/−4 cm$^{-1}$. Generally relatively pure crystalline Form III erlotinib has an XRPD that substantially corresponds to FIG. 3A and/or an FT-IR that substantially corresponds to FIG. 3C.

A DSC scan of Form III shows overlapping evaporation effects and melting around 154-156° C. TGA clearly showed a single step, corresponding to about 1 equivalent of water. Form III may be present as rectangular or square-like thin plates.

The hydrated crystalline erlotinib free base may be crystallized from a solvent comprising water. Preferably a water/ethanol/acetone mixture (2:1:1 V/V/V) at ambient temperature may be used which results in the hydrated Form I, preferably in pure Form I. Pure Form I should be understood as substantially free of any other crystalline forms of erlotinib. Pure Form III can be obtained by crystallizing from acetone/water (3:10 V/V) at ambient temperature. Pure Form III should be understood as substantially free of any other crystalline form of erlotinib.

The starting erlotinib used to prepare the crystalline erlotinib free base of the invention, can be obtained by any suitable or known means. The erlotinib can be obtained as an oil, an amorphous solid or as a crystalline material (such as a mixture of crystalline Forms) directly from the erlotinib synthesis and then dissolved into an appropriate solvent for (re) crystallization. Alternatively, the erlotinib free base can be liberated from an acid salt of erlotinib such as a hydrochloric acid or methanesulfonic acid salt of erlotinib, under aqueous basic conditions followed by an extraction of the free base with a water immiscible organic solvent, for instance ethyl acetate. The free base can be recovered as an oil or solid and then, if necessary, dissolved into a suitable solvent for (re) crystallization The hydrates of the invention can be converted into anhydrous forms and vice versa. For instance, any of the hydrates provides for the erlotinib free base Form II by heating.

The transition of hydrate Form I into Form II proceeds via melting of Form I after which the melt recrystallizes to Form II. The transition of Form III into Form II occurs via the solid-solid transformation. Form II appears to be the thermodynamically most stable form.

Another way to convert the hydrates to Form II includes recrystallization in a suitable solvent, preferably with some provision for removing water; e.g. by a Dean-Stark trap. Suitable solvents are for instance 2-propanol, chloroform, 1,4-dioxane, and mixtures thereof. Seeding can be used to speed up the crystallization rate.

Crystalline Forms I, II, and III are stable crystalline Forms which make them suitable for formulation of pharmaceutical compositions and for handling and storage, either individually or in combinations, e.g. a mixture of crystalline forms. Form II is generally considered the preferred form for making a pharmaceutical dosage form.

The invention also relates to the use of crystalline erlotinib free base, especially Form I, II, and/or III and their pharmaceutical compositions as a medicament. Generally the compound is used for the treatment of a hyperproliferative disease, especially a cancer. Specific cancers include brain, squamous cell, bladder, gastric, pancreatic, hepatic, glioblastoma multiform, head, neck, esophageal, prostate, colorectal, lung especially non-small cell lung cancer (NSCLC), renal, kidney, ovarian, gynecological, thyroid, and refractory cancers. Suitable dosage regimens comprise from 0.001 to 100 mg/kg/day.

The pharmaceutical composition can be in the form for enteral, parenteral or transdermal administration. The composition can be administered orally in the form of tablets, capsules, solutions, suspensions or emulsions. The composition can also be administered in the form of an injection solution or suspension or infusion solution, or transdermally with for instance a patch. Pharmaceutical compositions can be obtained in a way which is common for a person skilled in the art.

The compositions comprise a crystalline erlotinib and at least one pharmaceutically acceptable excipient. Finished dosage forms, such as tablets or capsules, generally contain at least a therapeutically effective amount of crystalline erlotinib and a suitable carrier.

Suitable carriers are for instance solid inert diluents or fillers or liquids such as water, alcohols, etc. Examples of common types of carriers/diluents include various polymers, waxes, calcium phosphates, sugars, etc. Polymers include cellulose and cellulose derivatives such as HPMC, hydroxypropyl cellulose, hydroxyethyl cellulose, microcrystalline cellulose, carboxymethylcellulose, sodium carboxymethylcellulose, calcium carboxymethylcellulose, and ethylcellulose; polyvinylpyrrolidones; polyethylenoxides; polyalkylene glycols such as polyethylene glycol and polypropylene glycol; and polyacrylic acids including their copolymers and crosslinked polymers thereof, e.g., Carbopol® (B.F. Goodrich), Eudragit® (Rohm), polycarbophil, and chitosan polymers. Waxes include white beeswax, microcrystalline wax, carnauba wax, hydrogenated castor oil, glyceryl behenate, glycerylpalmito stearate, and saturated polyglycolized glycerate. Calcium phosphates include dibasic calcium phosphate, anhydrous dibasic calcium phosphate, and tribasic calcium phosphate. Sugars include simple sugars, such as lactose, maltose, mannitol, fructose, sorbitol, saccharose, xylitol, isomaltose, and glucose, as well as complex sugars (polysaccharides), such as maltodextrin, amylodextrin, starches, and modified starches.

Furthermore the compositions may contain additional additives including stabilizers, preservatives, flavoring agents, colorants, lubricants, emulsifiers or other additives which will be apparent for the skilled persons in the art of preparing pharmaceutical compositions.

Crystalline erlotinib free base can also be used for the synthesis of a pharmaceutical acceptable salt of erlotinib. The compound may react in a solvent with an organic or inorganic acid followed by isolation of the pharmaceutical acceptable salt of erlotinib, generally by precipitation from the reaction mixture.

Suitable organic acids are methanesulfonic acid, naphthalene sulfonic acid, maleic acid, acetic acid, malic acid, fumaric acid, and citric acid. Suitable inorganic acids are hydrobromic and hydrochloric acid. Preferably the acid is methanesulfonic acid or hydrochloric acid. The salts of erlotinib may be obtained in anhydrous, hydrated or solvated forms. Preferably the erlotinib salts are obtained in solid form. More preferably the erlotinib salts are obtained in crystalline form.

The following examples are illustrative to the present invention. They are not intended to limit the scope of the invention in any manner.

EXAMPLES

Example 1

Erlotinib Form II 0.2 g of erlotinib monohydrate Form I was dissolved in 5 ml of 2-propanol at reflux. The solution was allowed to cool to R.T. and stirred at R.T. for about 19 hours; crystallization already occurred within the first hour of stirring. The solid was isolated by filtration over a P3-glass filter (reduced pressure) and air dried at R.T. and under ambient conditions for a few hours. An off-white powder with a yield of 140 mg was obtained. (analytical data in FIGS. 1A, 1B, and 1C)

Example II

Erlotinib Monohydrate Form I 3.0 g of erlotinib hydrochloride was suspended in 400 ml of demi-water/ethyl acetate (1:1 V/V) at R.T. To the suspension/emulsion, vigorously stirred at R.T., 300 mg of NaOH dissolved in 50 ml of demi-water was added very slowly (dropwise, >1 equivalent of OH$^-$). As a result of this, the HCl was removed from the drug substance and the drug substance was extracted into the organic phase. Some extra NaOH was added as the water-layer proved to be hardly basic afterwards and to ensure complete removal of HCl from the drug substance. The organic phase was twice washed with water and filtered over a P3-glass filter (reduced pressure), packed with prewashed Celite 545. The filtrate was dried with sodium sulphate for 15-30 minutes. The solution was filtered over a P3-glass filter (reduced pressure) to remove the sodium sulphate. Then, the solvent was evaporated under vacuum to dryness, yielding a pale beige, crystalline solid with a yield of approximately 1.85 g. (analytical data in FIGS. 2A, 2B, and 2C)

Example 3

Erlotinib Monohydrate Form III 0.2 g of erlotinib was dissolved in 15 ml of acetone at R.T. The solution was filtered over a P3-glass filter (reduced pressure) to remove foreign particles. To the clear filtrate, stirred at R.T., 50 ml of demi-water was added dropwise. During addition of water, fast crystallization occurred. The suspension was stirred at R.T. for about 2 minutes. The solid was isolated by filtration over a P3-glass filter (reduced pressure) and air dried overnight at R.T. and under ambient conditions. An off-white, fluffy to foamy powder mass was obtained. The yield was 150 mg. (analytical data in FIGS. 3A, 3B, and 3C)

Example 4

Erlotinib Monohydrate Form I 0.2 g of erlotinib form II was mixed together with 20 ml of demi-water. The suspension was refluxed, but the drug substance did not dissolve. To the hot suspension, 10 ml of ethanol was added, but no clear solution was obtained upon reflux. 10 ml of acetone was added to the suspension. After additional reflux, a clear solution was obtained. The solution was allowed to cool to R.T. and stirred at R.T. for about 23 hours; crystallization occurred. The suspension was stirred for a few minutes at 0° C. The solid was isolated by filtration over a P3-glass filter (reduced pressure) and air dried at R.T. and under ambient conditions for about 3 days. An off-white, nicely flowable powder of small and shiny crystals was obtained. The yield was 160 mg.

Example 5

Erlotinib Form II 1.5 g of erlotinib hydrochloride was suspended in 100 ml of demi-water/dichloromethane (1:1 V/V) at R.T. To the suspension/emulsion, vigorously stirred at R.T., 300 mg of NaOH dissolved in about 10 ml of demi-water was added slowly. As a result of this, the HCl was removed from the drug substance and the drug substance was extracted into the organic phase. Some extra 1M NaOH (few ml) and 50 ml of dichloromethane were added as extraction appeared to be far incomplete (solid material remained in the water phase).

After vigorous stirring at R.T. for 1 hour, both liquid layers appeared to be more or less clear. The organic layer was separated. Possible remaining drug substance in the water phase was extracted with an additional 50 ml of dichloromethane. The combined organic phases were filtered over a P3-glass filter (reduced pressure, packed with Celite 545), washed with 50 ml of fresh demi-water and filtered over the same filter again. The clear filtrate was dried with sodium sulphate for 1.5 hours (stirring). The solution was filtered over a P3-glass filter (reduced pressure) to remove the sodium sulphate. Then, the solvent was slowly evaporated under vacuum to dryness, yielding an off-white to pale beige, crystalline solid. No yield was determined.

Example 6

0.2 g of erlotinib monohydrate Form I was dissolved in 10 ml of acetone at R.T. and by means of stirring. To the solution, 150 µl of 2-propanol with 5-6 N HCl was added (>1 equivalent of HCl), while stirring was continued. As a result of this, immediate precipitation took place. The suspension was stirred at R.T. for an additional few minutes. The solid was isolated by filtration over a P3-glass filter (reduced pressure, rapid) and air dried overnight at R.T. and under ambient conditions. Lumps of off-white, sticky powder were obtained. The yield was 150 mg.

Erlotinib hydrochloride was obtained as a mixture of Form A and Form B.

Comparative Example

Based on Example 20 of WO 96/30347

37 mg of 3-ethynylaniline and 90 mg of 4-chloro-6,7-bis-(2-methoxy-ethoxy)quinazoline were added to a mixture of 1.5 ml of isopropanol and 25 µl pyridine. The resulting mixture was refluxed for 4 hours under an atmosphere of dry nitrogen. During reflux the color changed from pale yellow to orange-pink. The solvent was removed in vacuo on a rotavap (water bath 40° C.) The residue was partitioned between 5 ml 10% methanol in chloroform and 5 ml saturated aqueous NaHCO$_3$. The organic layer was dried over Na$_2$SO$_4$, filtered and concentrated in vacuo. The residue was dissolved in a mixture of 2.5 ml of acetone and 2.5 ml hexane and flash chromatographed on silica using 30% acetone in hexane, concentrated in vacuo on a rotavap (water bath 40° C.) About 90 mg of a sticky pale yellow solid was obtained (attached to the wall of the flask) The solid was analyzed on XRPD and the results shown in FIG. 4.

Each of the patents, patent applications, and journal articles mentioned above are incorporated herein by reference. The invention having been described it will be obvious that the same may be varied in many ways and all such modifications are contemplated as being within the scope of the invention as defined by the following claims.

What is claimed is:

1. A crystalline erlotinib free base which is substantially Form I, Form II, or Form III;
    wherein said crystalline Form I has an XRPD pattern that substantially corresponds to FIG. 2A;
    wherein said crystalline Form II has an XRPD pattern that substantially corresponds to FIG. 1A; and
    wherein said crystalline Form III has an XRPD pattern that substantially corresponds to FIG. 3A.

2. The crystalline erlotinib according to claim 1, wherein said Form is substantially crystalline Form II.

3. The crystalline erlotinib according to claim 2, having an XRPD pattern that substantially corresponds to FIG. 1A and an FT-IR spectrum that substantially corresponds to FIG. 1C.

4. The crystalline erlotinib according to claim 1, wherein said Form is substantially crystalline Form I.

5. The crystalline erlotinib according to claim 4, having an XRPD pattern that substantially corresponds to FIG. 2A and an FT-IR spectrum that substantially corresponds to FIG. 2C.

6. The crystalline erlotinib according to claim 1, wherein said Form is substantially crystalline Form III.

7. The crystalline erlotinib according to claim 6, having an XRPD pattern that substantially corresponds to FIG. 3A and an FT-IR spectrum that substantially corresponds to FIG. 3C.

8. A pharmaceutical composition comprising the crystalline erlotinib according to claim 1 and a pharmaceutically acceptable excipient.

9. The pharmaceutical composition according to claim 8, wherein said crystalline erlotinib is Form II.

10. A process, which comprises precipitating from a solution that comprises erlotinib dissolved in a solvent, a crystalline erlotinib free base according to claim 1, wherein said solvent is selected from methanol, ethanol, isopropanol, acetone, acetonitrile, chloroform, 1,4-dioxane, toluene, and mixtures thereof.

11. The process according to claim 10, wherein water is additionally present in said solvent and wherein said crystalline erlotinib free base is Form I or Form III.

12. The process according to claim 10, which further comprises converting said crystalline erlotinib free base into a pharmaceutically acceptable erlotinib salt.

13. The process according to claim 12, wherein said pharmaceutically acceptable salt of erlotinib is erlotinib hydrochloride or erlotinib methanesulfonate.

14. A method of treating cancer, which comprises administering an effective amount of the crystalline erlotinib free base according to claim 1 to a cancer patient in need thereof.

* * * * *